US008221406B2

(12) United States Patent
Desinger et al.

(10) Patent No.: US 8,221,406 B2
(45) Date of Patent: Jul. 17, 2012

(54) DEVICE FOR THE ELECTRO-SURGICAL SCLEROSING OF BODY TISSUES

(75) Inventors: Kai Desinger, Berlin (DE); Thomas Stein, Teltow (DE); André Roggan, Berlin (DE); Thomas Prezewowsky, Teltow (DE)

(73) Assignee: Celon AG Medical Instruments (DE)

( * ) Notice: Subject to any disclaimer, the term of this patent is extended or adjusted under 35 U.S.C. 154(b) by 899 days.

(21) Appl. No.: 11/660,613

(22) PCT Filed: Aug. 19, 2005

(86) PCT No.: PCT/EP2005/054107
§ 371 (c)(1),
(2), (4) Date: Sep. 29, 2008

(87) PCT Pub. No.: WO2006/021550
PCT Pub. Date: Mar. 2, 2006

(65) Prior Publication Data
US 2009/0234351 A1     Sep. 17, 2009

(30) Foreign Application Priority Data

Aug. 20, 2004   (DE) .................. 10 2004 041 681

(51) Int. Cl.
*A61B 18/04*          (2006.01)
(52) U.S. Cl. .......................................... 606/34
(58) Field of Classification Search ............. 606/34–41, 606/45, 48–50
See application file for complete search history.

(56) References Cited

U.S. PATENT DOCUMENTS

| 4,474,179 A | 10/1984 | Koch |
| 5,423,808 A | 6/1995 | Edwards et al. |
| 5,540,684 A | 7/1996 | Hassler |
| 5,630,426 A | 5/1997 | Eggers et al. |
| 6,228,080 B1 | 5/2001 | Gines |
| 6,739,349 B2 | 5/2004 | Kastenschmidt et al. |

(Continued)

FOREIGN PATENT DOCUMENTS

DE          31 20 102          5/1981

(Continued)

OTHER PUBLICATIONS

Office Action issued by the Japanese Patent Office on Sep. 10, 2010 in connection with corresponding Japanese Patent Application No. 2007-526469.

(Continued)

*Primary Examiner* — Christopher D Koharski
(74) *Attorney, Agent, or Firm* — Ostrolenk Faber LLP (57) ABSTRACT

A high frequency current application apparatus for thermal sclerosing of body tissue, comprising a high frequency generator connected to at least two electrodes, one of which is to be introduced into body tissue. The apparatus includes a measuring and calculating device adapted to ascertain impedance (or ohmic resistance) between the two electrodes between which a respective therapeutic high frequency current flows. A control device is connected to the measuring and calculating device for varying the output power. During high frequency current application the measuring and calculating device forms the first derivative with respect of time of the impedance. The control device reduces output power when that derivative exceeds a positive threshold characteristic of a threat of tissue desiccation and restores output power to the original power when the first derivative exceeds in positive values a negative threshold characteristic of adequate rehydration of body tissue.

36 Claims, 6 Drawing Sheets

U.S. PATENT DOCUMENTS

| | | |
|---|---|---|
| 2002/0151884 A1 | 10/2002 | Hoey et al. |
| 2003/0130711 A1 | 7/2003 | Pearson et al. |
| 2006/0015095 A1 | 1/2006 | Desinger et al. |

FOREIGN PATENT DOCUMENTS

| | | |
|---|---|---|
| DE | G 92 90 164.6 | 10/1992 |
| DE | 195 41 566 | 11/1995 |
| DE | 298 05 534 | 3/1998 |
| DE | 102 24 154 | 5/2002 |
| DE | 695 23 517 T2 | 5/2002 |
| DE | 102 24 154 A1 | 12/2003 |
| EP | 1 197 184 A1 | 4/2002 |
| GB | 2213381 * | 8/1989 |
| WO | WO 94/24949 | 11/1994 |
| WO | WO 03/099372 | 12/2003 |

OTHER PUBLICATIONS

S. Nahum Goldberg, et al., Percutaneous Radiofrequency Tissue Ablation: Optimization of Pulsed-Radiofrequency Technique to Increase Coagulation Necrosis, JVIR, 1999; 10:907-916.

S. Nahum Goldberg, Radiofrequency tumor ablation: principles and techniques, European Journal of Ultrasound 13 (2001) 129-147.

International Search Report, Aug. 12, 2005.

* cited by examiner

DEVICE FOR THE ELECTRO-SURGICAL SCLEROSING OF BODY TISSUES

This application is a national stage filing of and claims priority to PCT/EP2005/054107, filed Aug. 19, 2005 and claims priority to German Patent Application 10 2004 041 681.8, filed Aug. 20, 2004.

The present invention concerns an apparatus for the application of a high frequency current for the thermal sclerosing of body tissue. The application apparatus includes at least two electrodes which in the situation of use are in contact with the body tissue and of which at least one electrode is introduced into the body tissue. The application apparatus also includes a high frequency generator for producing a high frequency voltage, which is connected to at least two of the electrodes, a measuring device for measuring the impedance or the ohmic resistance between the selected electrodes, and a control device which when required changes the electrical output power of the high frequency generator and in a preferred variant can additionally control an external pump.

The output power of the high frequency generator is provided when the high frequency voltage at the outputs of the high frequency generator is delivered in the context of a high frequency current application to the electrodes which are in contact with the body tissue and it causes a high frequency current through the body tissue.

Electrosurgical and in particular electrothermal sclerosing of pathologically altered tissue, referred to hereinafter briefly as tissue or body tissue, is a method which is known in medicine. That method is of particular interest for the therapy of organ tumors, for example liver tumors. For the sclerosing procedure one or more electrodes are placed in the tissue to be sclerosed, that is to say the tumor tissue, or in the immediate proximity thereof, and an alternating current is caused to flow between the electrodes or an electrode and a neutral electrode externally fixed to the body. If the current flows between the electrode and the neutral electrode (optionally also between a plurality of electrodes and one or more neutral electrodes), that is referred to as a monopolar electrode arrangement. If in contrast the current flows between the electrodes which are disposed in the tissue themselves (in that case there must be at least two electrodes in the tissue), that is referred to as a bipolar arrangement. When there are more than two electrodes in the tissue, between which the alternating current flows alternately, that is referred to as a multipolar arrangement.

The applicators provided for placement in the tissue are generally in the form of electrode needles or flexible electrode catheters. Electrode needles have an electrically conducting cylindrical shank which, with the exception of one or more distal regions, the so-called active regions which respectively form an (active) electrode, is electrically insulated in relation to the surrounding tissue. Flexible electrode catheters have a flexurally soft, non-conducting shank and one or more distal active regions which each form a respective (active) electrode. The active electrodes are electrically conductively connected to the body tissue. Optionally the active electrodes are also equipped with integrated thermal sensors. In special design configurations further active electrodes can be mechanically extended at the distal end of the shank in order to enlarge the volume of tissue to which therapy can be applied.

In order to improve the efficiency of the treatment, applicators with electrode needles are also known, which have an internal closed cooling circuit operated by an external pump (internal cooling). Also known are electrode needles which in their distal region have one or more openings in order to introduce small amounts of fluid into the body tissue to be treated, by means of an external pump (open flushing).

In the monopolar arrangement a current flow is induced between the active electrodes and the neutral electrode or electrodes by means of a high frequency generator. In the alternative bipolar arrangement it is possible to dispense with the neutral electrodes. In that case the circuit is closed by way of a further active electrode, wherein the required active electrodes can be arranged in a coaxial arrangement in mutually insulated relationship on the electrode needle or on two separate electrode needles.

The alternating current applied by way of the electrodes is converted into Joule effect by the ohmic tissue resistance which is a part of the complex tissue impedance. At temperatures between 50° C. and 100° C. massive denaturing of the body-specific proteins occurs (coagulation) and as a consequence the areas of tissue involved die off. By virtue of the high current density at the active electrodes the heating effect takes place predominantly in the region of those electrodes so that local thermal tumor destruction is possible.

An apparatus for and a method of electrothermal sclerosing of pathological tissue is disclosed for example in U.S. Pat. No. 5,630,426.

What is decisive for effective and in particular reliable therapy is the production of a thermal destruction zone which is optimally adapted to the extent of the pathological tissue, that is to say the tumor tissue.

A further development of monopolar or bipolar tissue sclerosing is described in PCT/EP03/05439 in which more than two electrodes are introduced into the body tissue and in each case at least two electrodes are supplied with high frequency voltage by means of a selector device, for a given interval of time. In that case the selection of suitable electrode pairings is effected on the basis of the impedance measured between all possible electrode pairings or the measured ohmic resistance. That arrangement is particularly advantageous because even large volumes of tissue can be particularly effectively thermally sclerosed therewith, which permits for example reliable tumor therapy.

It is a known fact that the impedance or ohmic tissue resistance depends greatly on the progress of thermal tissue destruction, for which reason those parameters can be used for therapy control. Thus impedance and ohmic tissue resistance exhibit a typical pattern in respect of time in the course of tissue sclerosing.

When two electrodes are brought into body contact, an impedance value or ohmic resistance value initially occurs, which depends both on the electrode geometry (surface) and the electrode spacing, and is also influenced by the tissue between the electrodes and the conductivity of the tissue. In addition, consideration is to be given to the fact that, when viewing the tissue impedance, additional capacitive and inductive influences due to the connecting cables between the high frequency generator and the electrodes are also to be taken into account. That makes it difficult to provide precise regulation of the coagulation procedure. That makes in particular the ohmic resistance into a parameter which is almost free of such parasitic influences and which can therefore be used to greater advantage than impedance for the regulation of coagulation. Without limiting the idea of the invention, reference will be made hereinafter only to the resistance as the proposed apparatus can make use of both impedance and also ohmic resistance for therapy control.

After activation of the high frequency voltage at least two electrodes, between which body tissue is in electrical contact, the tissue resistance initially falls significantly below the starting value. That is due to the incipient increase in temperature of the tissue and the better mobility that this entails of the ions affording the electrical flow of current in the body tissue (for example $Na^+$, $Cl^-$). In addition with a further rise in temperature that involves ruptures of the cell membrane and thus also increased conductivity of the ions providing the current flow.

When however a temperature of about 100° C. is reached in the body tissue the tissue water begins to change over into the vapor phase. In that respect the precise temperature of the boiling point depends on the pressure which can be built up in the tissue before the vapor can escape and typically is not substantially above 100° C. By virtue of the expansion which is linked to the change in the water from the liquid phase to the vapor phase the vapor escapes through gaps in the tissue from the regions near the electrodes, in which typically the highest temperatures are to be recorded. This so-called vaporisation is therefore accompanied by a reduction in the water content in those regions near the electrodes, so that the tissue gradually suffers from a desiccation effect. Initially the remaining cell water which has remained in the regions near the electrodes is still sufficient to ensure mobility of the ions providing the current flow, but with an increasing degree of tissue desiccation the mobility of the ions becomes more and more restricted. That is the moment at which the tissue resistance rises significantly.

Accordingly there is then a kind of chain reaction in which the increase in resistance which occurs near the electrodes and which is caused by the tissue drying out, in relation to the overall electrical current distribution, with the output power remaining the same, causes more energy to be converted in those regions near the electrodes so that vaporisation and thus also the desiccation effect are accelerated. As a consequence an exponential rise in resistance is to be recorded.

As is known the procedure described above has an adverse effect on the actual therapy measure of tissue sclerosing because early onset of the desiccation effect, particularly when very high power densities are involved, prevents the propagation of an adequate, that is to say large-volume, thermal destruction zone. That is due to the fact that high frequency generators in accordance with the state of the art follow a power characteristic curve which permits optimum power delivery only in a given impedance or resistance range (the adaptation situation). If the impedances or ohmic resistances are outside that range, which is the case for example with a tissue desiccation effect near electrodes, then sufficient power can no longer be delivered to the tissue and the sclerosing operation comes to a halt. That however is to be prevented under all circumstances because otherwise incomplete tumor therapy could be the result, with the risk of recurrence of the disease at the same location.

To a limited extent internally cooled applicators can delay the desiccation process by virtue of their lower tissue contact temperature, but not to the extent as would be required for efficient therapy. Electrode needles involving open flushing also delay the onset of the desiccation effect, by fluid being subsequently supplied to the desiccation region continuously by the external pump. It will be noted however that this method has not proved its worth in practice as the uncontrolled introduction of fluid, in particular into tumor tissue, can involve a considerable cell displacement risk.

In order to prevent premature tissue desiccation, the high frequency generators according to the state of the art therefore provide for selecting an output power which excludes premature desiccation but which on the other hand is also sufficient to implement tissue sclerosing in a suitable time. It will be noted however that in clinical routine that is found to be extremely problematical because ultimately each tissue has quite specific properties which per se are not known to the person performing the therapy. Besides the physical parameters of specific tissue resistance, thermal conductivity and thermal capacity, those tissue properties include in particular the local blood flow which, by virtue of its cooling action, crucially contributes to determining the sclerosing process.

Accordingly mismatched power adjustment very frequently occurs in clinical practice. That either results in an unnecessary prolongation of the therapy when an excessively low level of power is involved or however, with the substantially more critical situation of using an excessive level of power, that results in the therapy being premature broken off, because of the rise in resistance caused by tissue desiccation. The only possible way of nonetheless still successfully terminating the therapy involves interrupting the delivery of power for a given period of time after tissue desiccation has been detected, until once again sufficient tissue fluid has collected in the regions near the electrodes.

More specifically if the power delivery is interrupted, the temperature very quickly falls below the vaporisation temperature because of the great temperature gradient so that vapor can condense at the electrodes. What is substantially more important however is the fact that, because of the low water content at the electrodes and the high water content in the surroundings, there is a steep gradient in respect of the water content so that water diffuses back relatively quickly and thus increases the local water content at the electrodes again. The resistance which after the interruption in power exhibits an exponentially falling configuration decreases to the same extent in order finally to become a constant value slightly below the original starting value, which signals adequate return diffusion of tissue water. It is however not known per se how long the process of return diffusion lasts until the constant resistance value is reached and continuation of the therapy with the renewed delivery of power is again possible.

In the event of poor, say excessively high, power preselection, the procedure involved in power interruption sometimes has to be repeated several times during a therapy procedure in order to be able to certainly terminate the therapy.

Apparatuses are already known which simplify the clinical procedure in a certain fashion. Thus for example Goldberg et al [Goldberg S N et al: Percutaneous radiofrequency tissue ablation: optimisation of pulsed-radiofrequency technique to increase coagulation necrosis; J Vas. Interv. Radiol 10(7): 907-16, 1999] describes an apparatus in which the impedance at the start of the sclerosing operation is measured and stored. As soon as the impedance exceeds the starting value by a fixed value in the course of sclerosing, the power is interrupted for a fixed period of time in order then automatically to resume the original starting value.

That method however suffers from crucial disadvantages. On the one hand, a fixed impedance threshold is assumed for triggering the power shutdown. That means however that the triggering sensitivity is dependent on the absolute value of the starting impedance. With low levels of starting impedance (for example in liver tissue) triggering can take place too late, while with high levels of starting impedance (for example in lung tissue) triggering in contrast thereto can take place too early because relatively small changes in impedance already lead to the triggering threshold being exceeded. That however impairs therapy efficiency because the phase without power delivery starts too early. A further disadvantage is the fact that the power must be interrupted for a fixed period of time after the fact that the impedance threshold has been exceeded is detected. Whether the time interval is sufficient to allow water to adequately diffuse back is not known. If the time interval were excessively long then therapy efficiency is lost while if it were too short desiccation begins again immediately and therapy efficiency is also lost.

The object of the present invention is to provide an apparatus which, with any possible impedance and resistance characteristics, permits optimum therapy efficiency and reliably prevents the tissue near electrodes from drying out.

That object is attained by a high frequency current application apparatus for thermal sclerosing of body tissue, which includes at least two electrodes in contact with the body tissue, of which at least one electrode is to be introduced into the body tissue. In the case of a bipolar or multipolar arrangement one or more bipolar applicators each having two electrodes on a shank or two or more applicators with only one electrode per shank are to be introduced into the tissue. In addition the application apparatus includes a high frequency generator for producing a high frequency voltage, which is connected to at least two of the electrodes, and a measuring and calculating device for measuring the impedance or the ohmic resistance between the selected electrodes. For the sake of simplification, both terms impedance and ohmic resistance are referred to for brevity as resistance hereinafter, without thereby restricting the idea of the invention. Furthermore the high frequency current application apparatus includes a control device for varying the electrical output power of the high frequency generator during a high frequency current application.

In a preferred embodiment the measuring and calculating device is adapted to ascertain the resistance between the two electrodes between which a respective therapeutic high frequency current flows, from at least two of the parameters of current strength, voltage, phase relationship and active power of the therapeutic high frequency current.

Preferably the two electrodes, between which impedance or ohmic resistance measurement is effected, are arranged on a shank which is to be introduced into the body tissue.

One of the two electrodes, between which impedance or ohmic resistance measurement is effected, can be a neutral electrode which is to be applied to the surface of the skin. Preferably that neutral electrode is formed from a plurality of separate elements which are to be applied to different surfaces of the skin and which are at the same electrical potential by virtue of an electrically conducting connection.

It is however also possible, for determining the tissue behaviour, to use a circuit which is separate from the therapeutic voltage source and which can also operate at a frequency other than the therapy frequency and which also evaluates a combination of the parameters of current strength, voltage, active power and phase characteristics to ascertain the resistance.

Now an essential feature of the apparatus is that it is not the absolute value of the resistance that is measured to detect tissue desiccation, but that its variation behaviour in respect of time is ascertained by evaluation of the first derivative of the resistance in respect of time. Accordingly detection of tissue desiccation becomes independent of the starting value of the resistance and can be used without limitation for different kinds of tissue, electrode geometries and electrode configurations.

In a preferred embodiment the measuring apparatus delivers a new respective result of resistance measurement at short time intervals of some milliseconds. The result of the preceding measurement is subtracted from that result for example by a microprocessor, and divided by the length of the time interval between two measurement operations. In that way the first derivative of the impedance or ohmic resistance is formed in the manner of a differential quotient as two respective measurement values for the impedance and the ohmic resistance respectively. If the result is positive and the value is above a predetermined threshold value (also referred to hereinafter, in particular in the specific description, as the limit value), which typically should be in the range of between 5 ohms/s and 50 ohms/s, the measuring device supplies a signal to the control device, to indicate that desiccation near the electrodes is immediately impending. The control device thereupon significantly reduces the output power in order to counteract desiccation.

The control device is preferably so designed that it continuously reduces the output power over a short period of time. A suitable period of time is between 0.1 and 5 seconds in length.

If the parameters which are evaluated for ascertaining the resistance are derived from the therapeutic high frequency current the reduced output power should be sufficiently low to prevent further tissue desiccation and to allow sufficient tissue water to flow back into the desiccation regions (the temperature at the electrodes should fall markedly below 100° C.). On the other hand the reduced output power should still be sufficiently great to still permit the resistance value to be reliably determined from the high frequency current. A typical value for the reduced output power is in the range of between 2% and 50% of the original output power. If in contrast the resistance is ascertained independently of the therapeutic high frequency current the output power can even be reduced to 0%.

If measurement of the resistance suffers from noise, which can be the case in particular when the parameters which are evaluated to ascertain the resistance are derived from the therapeutic high frequency current, it is appropriate for the measurement values to be subjected to averaging before calculation of the derivative is effected in order to avoid incorrect triggerings. For that purpose a suitable number of measurement values is totalled and the average value is calculated in known manner by division by the number of measurement values. A second measurement value is then advantageously determined in an identical manner. Calculation of the first derivative is now effected as described hereinbefore using the average values, in which case the time interval to be applied corresponds to the period of time which was required for determining an average value.

A further advantageous feature of the apparatus provides that, after reduction in the output power, measurement of the first derivative of the resistance in respect of time is also effected in the above-described manner. If the power is already reduced shortly thereafter tissue water again collects in the previously desiccated regions so that the resistance falls again until a constant value is reached in the proximity of the original starting value. That moment in time is characterised in that the first derivative of the variation in resistance in respect of time is initially negative and approaches the value zero. Accordingly the optimum moment in time is detected for setting the output power to its original value again.

That is preferably achieved in that the measuring device sends a signal to the control device when the first derivative of the variation in resistance is negative and is near zero in a small interval. A typical interval is −3 ohms/s to 0 ohm/s. In a corresponding fashion the measuring or calculating device, in conjunction with the control unit, is preferably adapted to respond thereto when the first derivative in respect of time of the impedance or ohmic resistance characteristic exceeds a value in the range of between −10 ohms/second to −0.1 ohm/second. Those values can be adjustable in dependence on the tissue to be treated. Thereupon the control device again regulates the output power of the high frequency current to the original starting value, wherein in the preferred embodiment the output value is increased over a short period of time of typically some tenths of a second in order to avoid unwanted sudden vaporisation effects.

The measuring and calculating device can either be part of the control device or it can be arranged outside the control device and connected to the control device (controller). The measuring and calculating device can also be embodied in two separate units, namely a measuring device with the calculating device connected downstream thereof, or an integrated measuring and calculating device.

A preferred variant is one in which the high frequency generator, the measuring and calculating device and the control device are disposed in a common housing.

In a preferred embodiment, after the reduction in output power with incipient desiccation the derivative of the resistance characteristic is not immediately further measured or evaluated, but firstly a compulsory waiting time (minimum time) with a reduced output power in the range of between 1 seconds and 10 seconds is observed. That is advantageous as, after the reduction in the output power, firstly a plateau of the resistance value is also measured because the return diffusion of water requires some time in order to cause the resistance to measurably fall again. In that way a constant resistance value is produced for a short period of time at a high level, which however is not to be confused with the constant value after return diffusion of the tissue water. Nonetheless that resistance plateau could trigger a faulty increase in the output power if the minimum waiting time is not observed, after which at any event a negative gradient in respect of the resistance characteristic occurs. After the expiry of the compulsory waiting time (minimum time) the control device again uses the first derivative in respect of time of the impedance characteristic for further control of the output power of the high frequency generator.

In a variant of the invention electrode needles with open flushing are used. A particular feature in that respect is that a pump which provides the flow of fluid into the tissue is initially not in operation, that is to say the applicator initially operates without open flushing. That means that the risk of the above-described cell displacement effect is avoided. As soon as the apparatus reduces the output power of the high frequency generator by virtue of detection of incipient desiccation, the control device sends an electrical signal to the pump by way of a control connection, to deliver a small fluid bolus into the desiccated tissue. That entails two advantages: on the one hand the amount of fluid can be measured in a preset manner in such a way that only the amount of fluid which was previously lost by desiccation is injected. That does not involve fluid-implemented cell displacement. Secondly, the process of rehydration is considerably accelerated thereby because it is not necessary to wait for natural return diffusion of tissue water so that the time for the original output power to be resumed is significantly reduced.

In a further embodiment the amount of the applied fluid bolus is not preset. Rather, as in the above-described variant, the pump is started by means of a start signal from the control device when tissue desiccation is impending. In that case, only a minimum flow of fluid is applied, which does not immediately result in an excessive accumulation of fluid. The application of fluid is now effected until the control device, in accordance with the invention, detects adequate rehydration of the tissue (by way of the first derivative of the resistance characteristic in respect of time) and delivers the signal for restoring the original output power. At that moment in time a stop signal is passed to the pump to terminate the transport of fluid. That procedure has the advantage that the additionally introduced fluid means that the waiting time until restoration of full power is reduced and at the same the amount of fluid is very accurately adapted to the actual need. More specifically, if the volume of tissue is completely rehydrated again, the tissue resistance assumes a constant characteristic and the pump switches off due to a stop signal from the control device. Accordingly the introduction of an excessive amount of fluid is prevented and the risk of cell displacement does not arise.

For implementation of that method the high frequency application apparatus has a control connection for an external pump which is connected to the electrodes introduced into the body tissue, to which connection there is preferably connected a pump which is adapted to convey fluid into body tissue to be treated. The control device is adapted to cause the pump to be switched on by the delivery of a start signal by way of the control connection when the control device detects a threat of tissue desiccation.

In that respect the control device is preferably adapted to actuate the external pump in such a way that fluid is conveyed into the treatment volume exclusively through those electrodes, between which the control device has detected a threat of tissue desiccation.

In addition, the pump is switched on and the output power is reduced—caused by the control unit—preferably simultaneously.

The pump is preferably adapted to operate with a constant delivery. If the high frequency application apparatus detects adequate rehydration the control device in a preferred variant switches the external pump off again. That is effected for example by the delivery of a stop signal by way of the control connection. Deactivation of the pump and restoration of the output power to the original power are preferably effected at the same moment in time.

The fluid used can be sterile physiological saline solution or sterile water.

The advantage of the present invention, besides the substantially easier and securer handling, is above all the effect that the maximum possible mean power is always automatically applied by the apparatus according to the invention at any moment in time in the therapy and over a very wide range of possible biological and physical parameters. That ensures that at any event operation is effected with the maximum efficiency, that is to say the shortest possible time is only ever required for a given amount of energy to be introduced.

There is no need for previous knowledge on the part of the user of the high frequency current application apparatus according to the invention. The sole prerequisite is that an adequate reference power is preset. Here it has proven appropriate in practice to select a power presetting which only depends on the sum of the surface areas or lengths of all electrodes introduced into the body tissue (larger electrode area signifies higher power setting, for example 0.2 watt/mm$^2$ or 1 watt/mm$^2$). In that respect the reference power is to be set somewhat higher than would be required at a maximum with the most detrimental combination of biological and physical parameters. That ensures that the described regulating function of the apparatus always takes place in the course of a therapy and can bring the mean power to the optimum value in that way.

The invention is described in greater detail hereinafter with reference to the accompanying Figures in which.

Figure 1A:
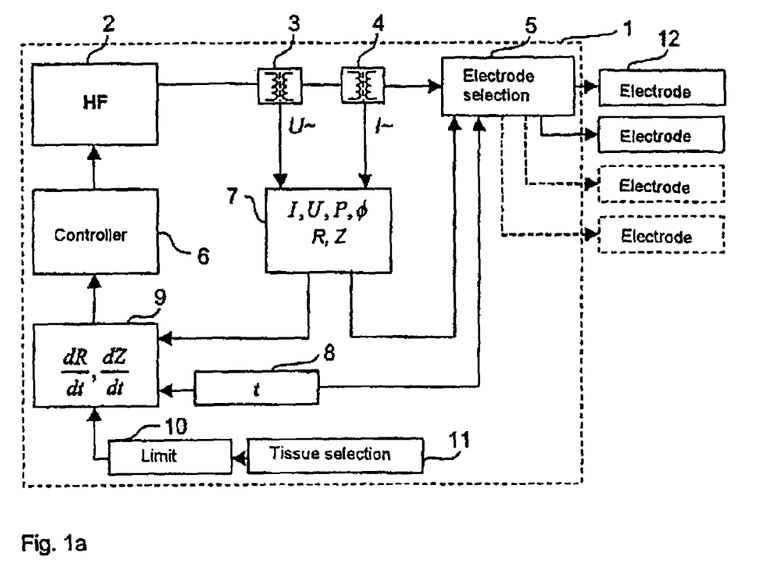
FIG. 1a shows a block diagram of the high frequency application apparatus according to the invention for the thermal sclerosing of body tissue.

FIG. 1a shows the high frequency application apparatus 1 for the thermal sclerosing of body tissue, comprising two electrodes 12 which are in contact with the body tissue. The high frequency application apparatus 1 is preferably disposed in a unit. The high frequency application apparatus 1 comprises a high frequency generator 2 for producing a high frequency voltage and a measuring device 7 for determining the impedance or the ohmic resistance between the electrodes 12.

In a preferred embodiment impedance or ohmic resistance is determined in the measuring device 7 by means of a high frequency transformer for the voltage 3 and for the current 4 in known manner from a combination of the parameters current strength, voltage, active power and phase characteristic of the therapeutic high frequency current.

Now an essential feature of the apparatus is that the absolute value of the impedance or ohmic resistance is not measured for detecting tissue desiccation, but its variation characteristic in respect of time (time measurement by means of a timer 8) is ascertained by evaluation of the first derivative of the resistance in a calculating device 9.

In a preferred embodiment the measuring device 7 produces a new respective result of resistance measurement at short time intervals of some milliseconds. The result of the preceding measurement is subtracted from that result for example by a microprocessor and divided by the length of the time interval between two measurement procedures, the length of the time interval being predetermined by a timer 8. If the result is positive and if the value is above a predetermined limit value 10 (upper threshold value) which can be optionally established prior to the therapy by means of a tissue selection device 11 and which should typically be in the range of between 5 ohms/s and 50 ohms/s the calculating device 9 supplies a signal to the control device 6, that desiccation near the electrodes is directly impending. The control device thereupon reduces the output power of the high frequency generator 2 significantly in order to counteract desiccation.

In a preferred embodiment the high frequency application apparatus 1 includes an electrode selection control unit 5 if more than two electrodes are to be operated in a multipolar mode of operation, in which case the electrode control unit 5 also uses the parameters of impedance or ohmic resistance as well as time in order to suitably actuate the electrodes.

Figure 1B:
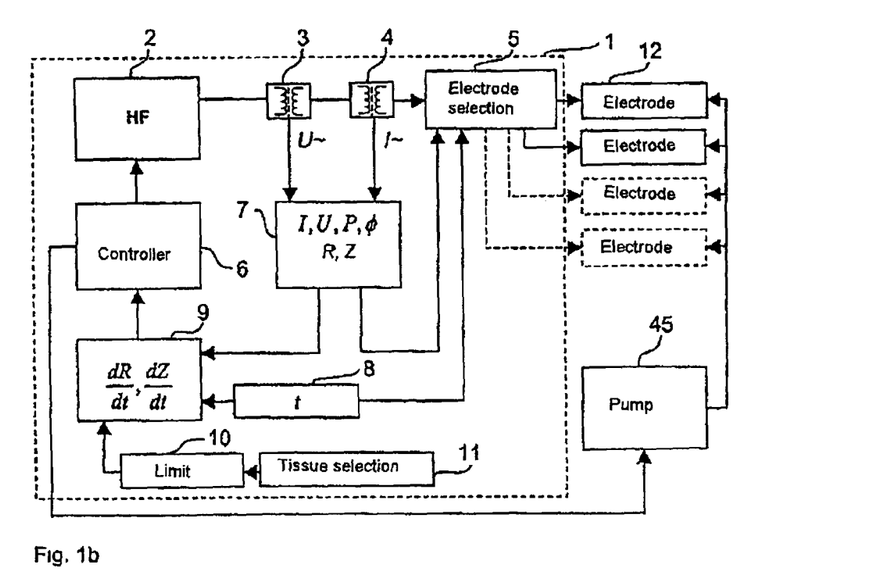
FIG. 1b shows a block diagram of the high frequency application apparatus according to the invention for the thermal sclerosing of body tissue with an external pump.

FIG. 1b shows a further embodiment of the high frequency application apparatus 1 described with reference to FIG. 1, with an external pump 45. As soon as the high frequency application apparatus 1 detects incipient desiccation the output power of the high frequency generator 2 is reduced and the control device 6 passes an electrical signal to the pump to deliver a preset small fluid bolus to the electrodes 12 and thus into the desiccation tissue.

In a preferred embodiment the pump 45 which is started by the control device 6 by means of a signal applies a flow of fluid until the control device 6 detects adequate rehydration of the tissue and delivers a signal for restoration of the original output power. At that moment in time a further signal is passed to the pump 45 to terminate fluid transport.

Figure 1C:
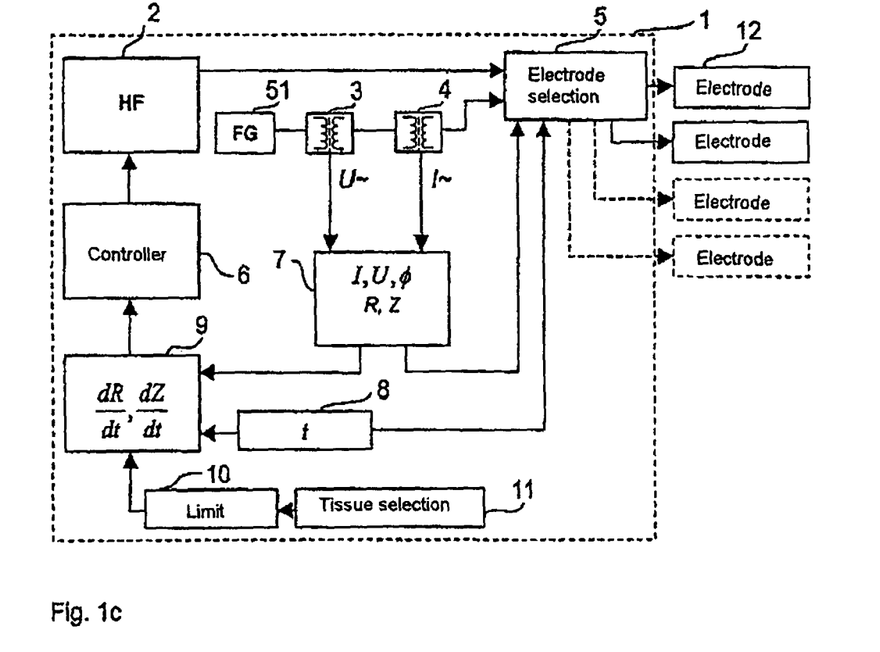
FIG. 1c shows a block diagram of the high frequency application apparatus according to the invention for the thermal sclerosing of body tissue having an independent circuit for ascertaining the parameters required impedance or ohmic resistance.

FIG. 1c shows an alternative embodiment in which the resistance is also ascertained independently of the therapeutic high frequency current by means of a separate frequency generator 51. With this arrangement there is no need to maintain the therapeutic high frequency current at a low level of power during the rehydration phase in order to ascertain measurement values of impedance or ohmic resistance. In this arrangement therefore, with incipient desiccation, the output power of the high frequency generator can also be entirely switched off. The measurement frequency and the measurement current are independent of the therapeutic high frequency current and for example can be so selected that both changes in tissue are detected in the optimum fashion and also there is no significant increase in temperature of the tissue in the measuring operation.

As shown in the graph 13 in FIG. 2 the impedance and the ohmic resistance 14 initially fall significantly below the starting value after activation of the high frequency voltage at two electrodes which are in electrical contact with the body tissue. That is due to the incipient rise in temperature of the tissue and the resulting better mobility of the ions affording the electrical current flow in the body tissue (for example $N^+$, $Cl^-$). Upon a rise in the temperature above 50° C. massive denaturing of the body-specific proteins (coagulation) 22 occurs and as a consequence that results in the affected areas of tissue dying off (see FIG. 3). That involves a gradual propagation of the coagulation 22. That is distinguished by a relative constant characteristic 15 in respect of the impedance or ohmic resistance.

Figure 3:
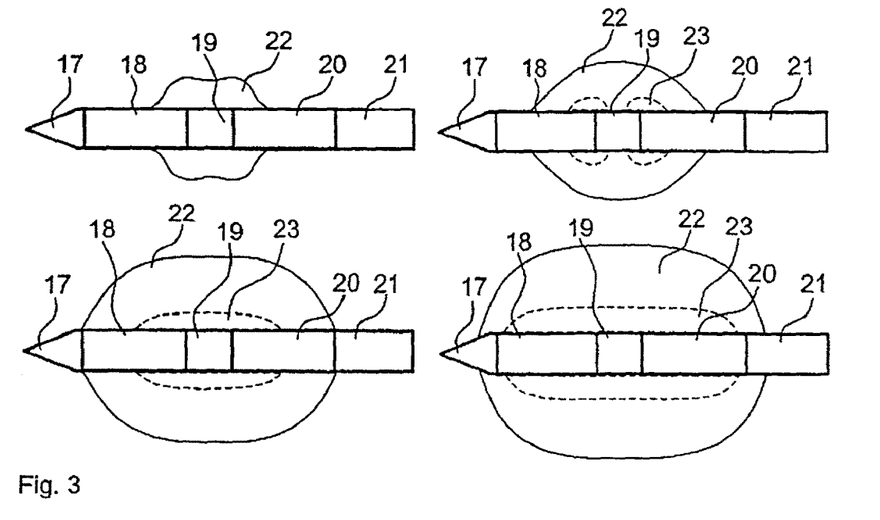
FIG. 3 shows a diagrammatic view in section by way of example of a bipolar arrangement having two electrodes on a shank during activation of the therapeutic high frequency current in the body tissue.

FIG. 3 shows by way of example the continuous spread of the above-indicated coagulation zone 22 in the body tissue in the region of the electrodes 18, 20 axially arranged on a shank 21 (the electrodes being electrically insulated from each other by an insulator 19) with progressive application in time of the high frequency current. The coagulation process begins in the adjoining body tissue which is established in the region of the mutually adjacent zones of the electrodes 18, 20. The coagulation area then spreads forwardly to the free tip 17 of the electrode arrangement and proximally towards the proximal end of the electrode 20.

With an increasing application time, a temperature of about 100° C. is reached in the body tissue and the tissue water begins to change into the vapor phase. By virtue of the expansion which is linked to the change of the water from the liquid phase into the vapor phase the vapor moves away through gaps in the tissue from the regions near the electrodes, in which typically the highest temperatures are to be recorded. That so-called vaporisation therefore entails a reduction in the water content in those regions near the electrode so that a desiccation zone 23 is gradually formed in the tissue, which finally extends over the length of both electrodes 18, 20. Initially the residual cell water which has remained in the regions near the electrodes is still sufficient to ensure mobility of the ions providing the current flow, but the mobility of the ions is restricted more and more with an increasing degree of desiccation. That is the moment in time at which the desiccation zone 23 encloses the entire area of the electrodes 18, 20 and the tissue resistance 16 (as shown in FIG. 2) significantly rises.

Figure 2:
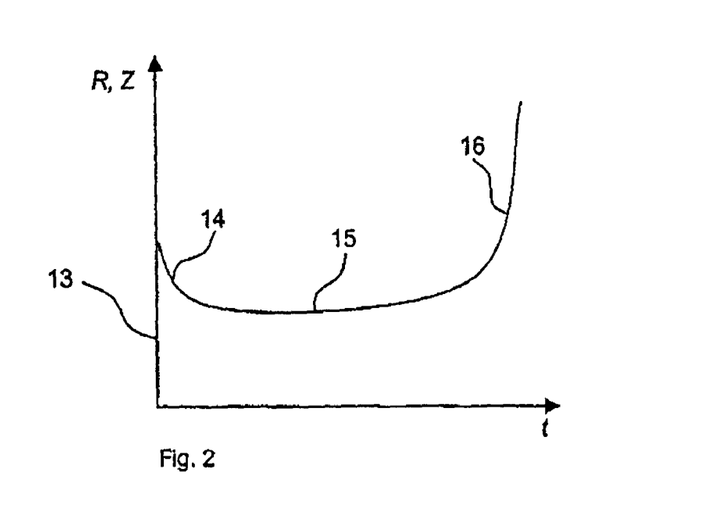
FIG. 2 shows a graph to represent the resistance characteristic between the electrodes of an applicator in dependence on the application time during the activation of the therapeutic high frequency current in the body tissue.
Figure 4A:
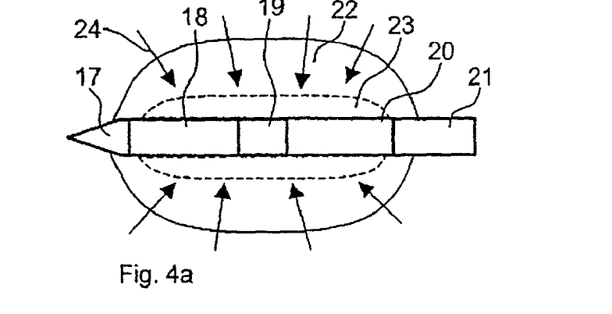
FIG. 4a shows a diagrammatic view in section by way of example of a bipolar arrangement having two electrodes on a shank during inactivation (return diffusion of the tissue water) of the therapeutic high frequency current in the body tissue.

Referring to FIG. 4a after a reduction in the output power return diffusion of the tissue water 24 into the previously desiccated region 23 takes place so that the resistance falls again until a constant value is reached in the proximity of the original plateau value 15 (as shown in FIG. 2).

Figure 4B:
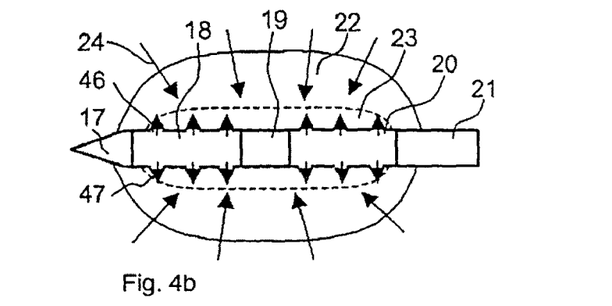
FIG. 4b shows a diagrammatic view in section by way of example of a bipolar arrangement having two open-flushed electrodes on a shank during inactivation (return diffusion of the tissue water and pumping in fluid) of the therapeutic high frequency current in the body tissue.

In the preferred embodiment of the invention shown in FIG. 4b electrodes 18 with open flushing are used. After the reduction in the output power fluid 47 is delivered through the openings 46 of the electrodes 18 into the previously desiccated region 23. Approximately the amount of fluid which was previously lost due to desiccation is delivered. In that way the process of rehydration of the tissue water 24 is considerably speeded up because it is not necessary to wait for natural return diffusion of tissue water 24 so that the resistance falls again and the time until restoration of the original output power takes place is significantly shortened.

Figure 5:
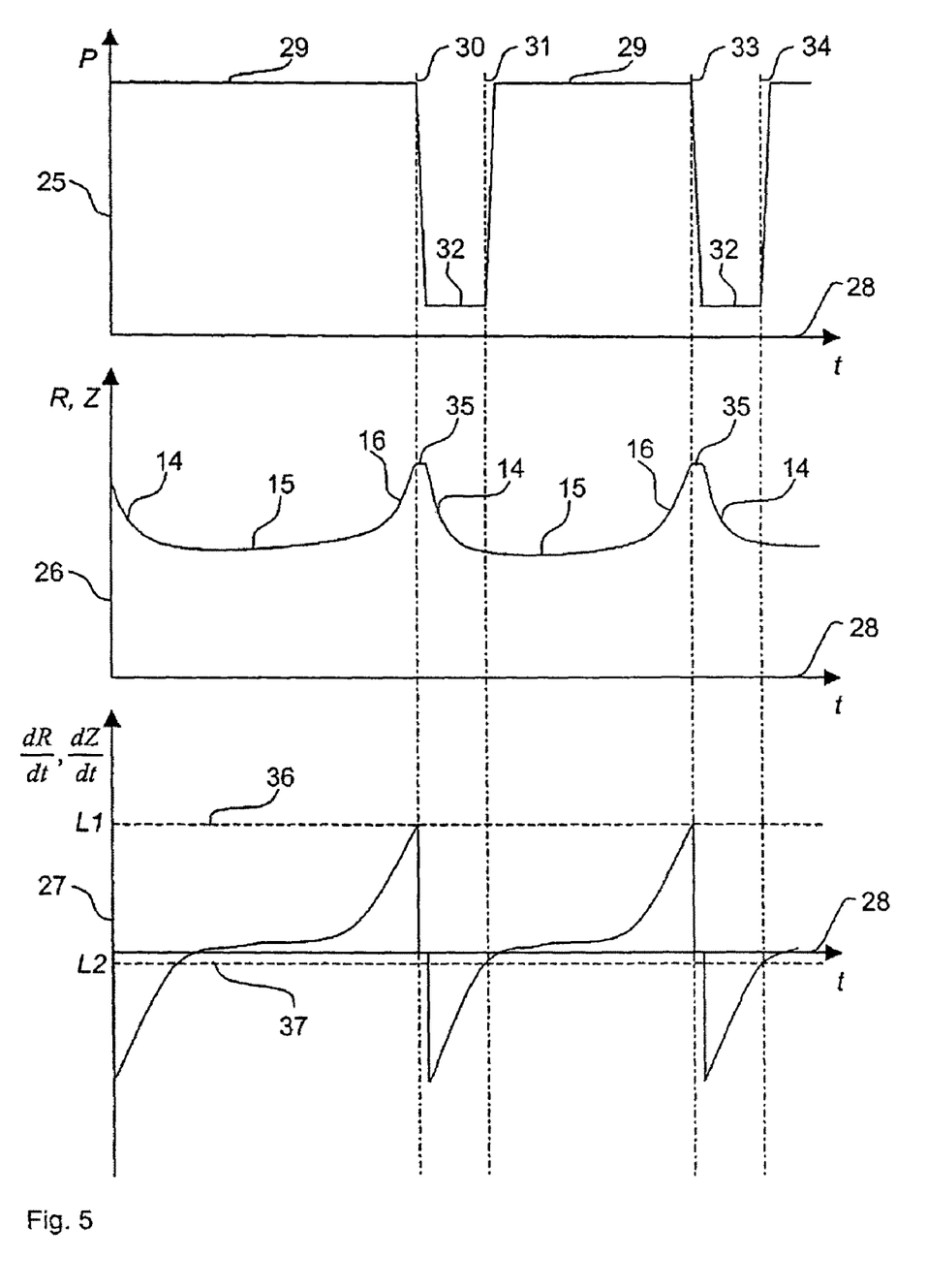
FIG. 5 shows graphs representing the output power, the resistance characteristic and the first derivative of the resistance characteristic in respect of time between two electrodes in dependence on the application time during activation of the therapeutic high frequency current in the body tissue.

FIG. 5 shows the typical characteristic in respect of time of the output power 25, impedance or ohmic resistance 26 and the derivative in respect of time of impedance or ohmic resistance 27 during the sclerosing of body tissue with the high frequency current application apparatus according to the invention.

After activation of the high frequency voltage the tissue resistance firstly falls significantly below the starting value (14), as shown in graph 26. With the output power remaining the same as shown in graph 27 there is firstly plateau formation 15 as described with reference to FIG. 2, with a following steady rise in the resistance until desiccation begins and the resistance rises exponentially (16).

The first derivative of the resistance characteristic 26 in respect of time, at the corresponding moments in time, initially involves negative values as shown in the graph 27, which approach the value zero in order then to move into the positive range. If the result is positive and the value is above a predetermined limit value 36 (upper threshold) which is established prior to the therapy then the calculating device 9 at the moment in time 30 delivers a signal to the control device 6 (see FIG. 1a) that desiccation near the electrodes is immediately impending. The output power as shown in graph 25 is immediately reduced in order to counteract desiccation. The resistance remains for a short time at the level 35 after the reduction in output power 32 because the return diffusion of water needs some time in order to cause the resistance to fall measurably again. If the power is already reduced shortly thereafter at 32 tissue water again collects in the previously desiccated regions so that the resistance falls again at 14 until a constant value is reached in the proximity of the original plateau value 15. That is characterised in that the first derivative of the resistance characteristic in respect of time is initially negative and then approaches a limit value 37 (lower threshold value) near zero. A typical value is −3 ohms/s to 0 ohm/s. In that way the optimum moment in time 31 is detected for restoring the output power to its original value again. That is achieved by the calculating device 9 sending a signal to the control device 6 (see FIG. 1a). Thereupon the control device regulates the output power of the high frequency current to the original starting value 29 again, wherein, in the preferred embodiment, the starting value is increased over a short period of time of typically some tenths of a second in order to avoid unwanted sudden vaporisation effects. The described process can then be repeated as often as may be desired at irregular intervals (33, 34) until the therapy is manually interrupted.

Figure 6A:
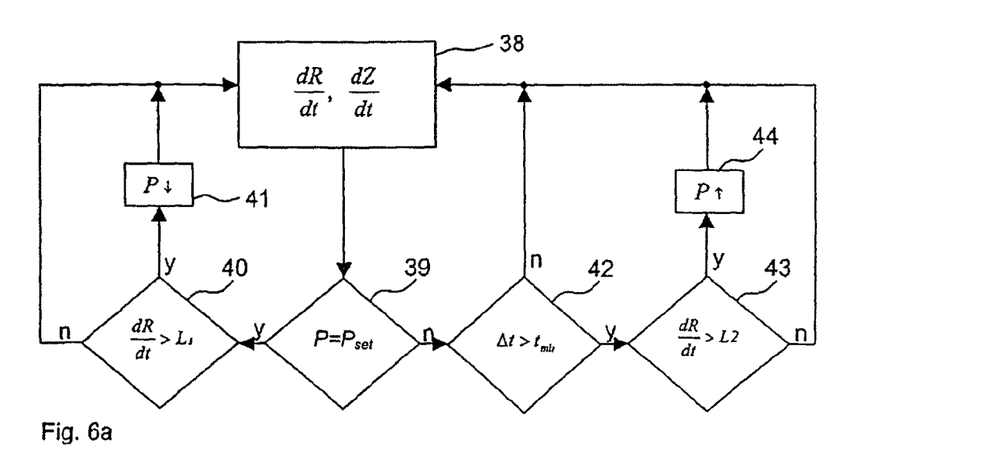
FIG. 6a shows a flow chart of the high frequency application apparatus according to the invention for the thermal sclerosing of body tissue.

FIG. 6a shows the mode of operation of the calculating device 9 from FIG. 1a, in the form of a flow chart. After the first derivative of the resistance in respect of time 38 is determined, the actual output power is compared to the set output power (39). If the output power is at the reference power 39, a check is made in a further step 40 to ascertain whether the value of the first derivative of the resistance in respect of time is above the predetermined limit value 36. If yes the order 41 is given to reduce the output power (32). If in contrast the first derivative of the resistance in respect of time is still below the predetermined limit value 36 (40), the next operation for determining the first derivative of the resistance in respect of time 38 is effected and the cycle is implemented afresh.

If in contrast it is established in 39 that the actual output power is already at the reduced level (32), a check is firstly made at 42 to ascertain whether the minimum waiting time was observed prior to possibly resetting the output power to the original reference value 29. If the minimum waiting time 42 were observed then the derivative of the resistance characteristic is compared in step 43 to the preset limit value 37. If the derivative should be greater than that limit value 37 the order 44 is given to set the output power to the reference value 29 again. If the minimum waiting time 42 were still not observed or if the derivative in respect of time of the resistance characteristic is still less than the limit value 37 the next operation of determining the first derivative in respect of time 38 is effected and the cycle is implemented afresh.

It was found to be advantageous to query a minimum waiting time 42 as, after the reduction in the output power 32, initially the plateau of the resistance value is also measured because return diffusion of water needs some time in order to cause the resistance value to measurably fall again. As a result for a short period of time there is a constant resistance value at a high level 35 which however is not to be confused with the constant value after return diffusion of the tissue water. Nonetheless that resistance plateau could trigger a faulty increase in the output power if the minimum waiting time 42 is not observed, preferably in the range of between 1 second and 10 seconds, after which at any event a negative gradient in respect of the resistance characteristic occurs.

Figure 6B:
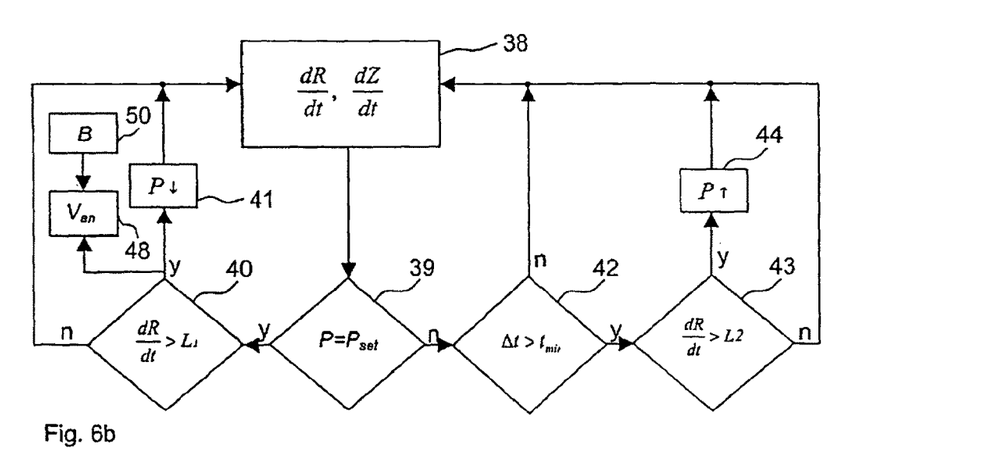
FIG. 6b shows a flow chart of an embodiment of the high frequency application apparatus according to the invention for the thermal sclerosing of body tissue with an external pump and with a presettable applied fluid bolus.

FIG. 6b shows a preferred embodiment of a flow chart of the mode of operation, described with reference to FIG. 6a, of the calculating device 9 shown in FIG. 1a. As soon as incipient desiccation of the tissue is detected, that is to say the value of the first derivative of the resistance in respect of time is above the predetermined limit value 36, the output power is reduced (41). At the same time a small fluid bolus is delivered (48), which can be preset by way of a device 50.

Figure 6C:
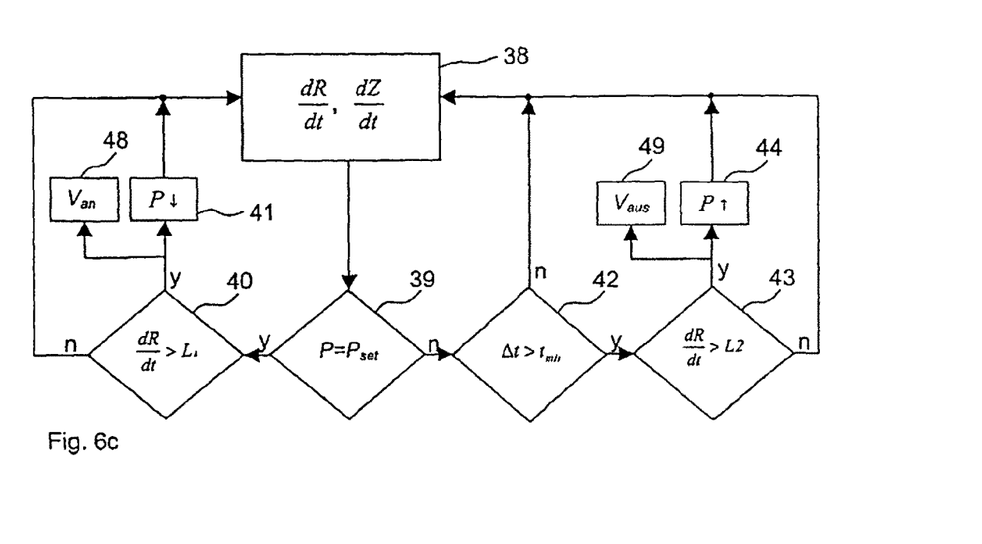
FIG. 6c shows a flow chart of an embodiment of the high frequency application apparatus according to the invention for the thermal sclerosing of body tissue with an external pump without a preset amount of the applied fluid bolus.

FIG. 6c shows a further preferred embodiment of an expanded flow chart of the mode of operation described with reference to FIG. 6a of the calculating device 9 shown in FIG. 1a. When incipient desiccation of the tissue is detected, that is to say the value of the first derivative of the resistance in respect of time is above the predetermined limit value 36, then the output power is reduced (41). At the same time a minimal fluid flow is started (48). That takes place until the derivative of the resistance characteristic in step 43 is greater than the preset limit value 37 and the output power (44) is re-set to the reference value 29. The fluid flow is stopped (49).

Figures 7A, 7B:
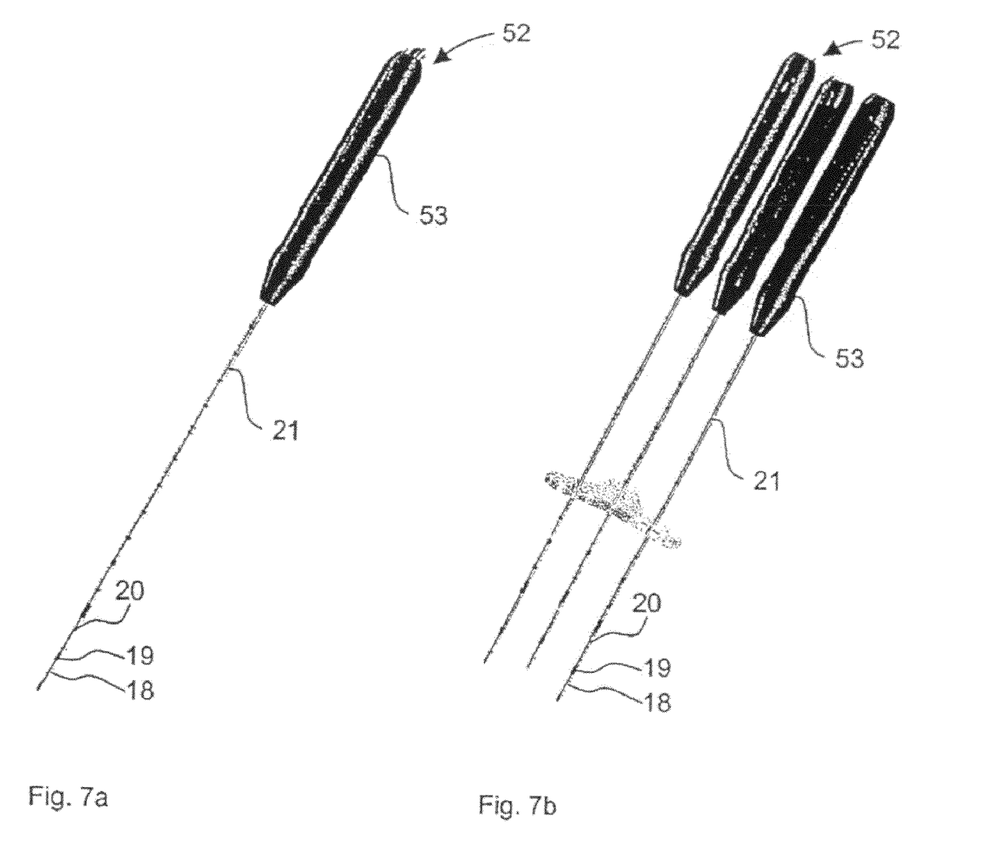
FIG. 7a shows a view by way of example of an applicator with a bipolar arrangement of two electrodes on a shank.
FIG. 7b shows a view by way of example of a plurality of applicators in a multipolar arrangement each having two electrodes on a shank per applicator.

FIG. 7a shows a preferred embodiment of an applicator with a bipolar arrangement of two electrodes on a shank. The applicator 52 comprises a handle 53 and a shank 21 which is connected to the handle and which has two electrodes 18, 20 which are arranged in mutually axial relationship (and which are electrically insulated from each other by an insulator 19).

FIG. 7b shows a further embodiment of a plurality of applicators in a multipolar arrangement each having two electrodes on a shank per applicator. The applicators 52 each comprise a handle 53 and a shank 21 which is connected to the handle and which has two mutually axially arranged electrodes 18, 20 (which are electrically insulated from each other by an insulator 19).

The invention claimed is:

1. A high frequency current application apparatus for thermal sclerosing of body tissue, comprising a high frequency generator to which there are connected at least two electrodes of which at least one electrode is to be introduced into body tissue, and a measuring and calculating device which is adapted to ascertain from at least two of the parameters current strength, voltage, phase relationship and active power the impedance or the ohmic resistance between the two electrodes, between which a therapeutic high frequency current respectively flows, or to ascertain same by means of a measuring circuit independent of the therapeutic circuit, and a control device connected to the measuring and calculating device for varying the electrical output power of the high frequency generator, characterised in that
the measuring and calculating device is adapted during a high frequency current application to form the first derivative from the characteristic in respect of time of the impedance or the ohmic resistance and to deliver a value dependent on the value of the first derivative, and
the control device is adapted to significantly reduce the output power when the signal of the measuring and calculating device indicates that the derivative in respect of time of the impedance or the ohmic resistance exceeds a positive threshold which is characteristic for a threatening tissue desiccation and
to restore the output power to the original power again when the signal of the measuring and calculating device indicates that the first derivative of the characteristic in respect of time of the impedance or ohmic resistance exceeds in the direction of positive values a negative threshold which is characteristic of adequate rehydration of the body tissue.

2. A high frequency current application apparatus as set forth in claim 1 characterised in that the measuring and calculating device is adapted to derive the parameters required for ascertaining impedance or ohmic resistance from a therapeutic high frequency current flowing between the electrodes.

3. A high frequency current application apparatus as set forth in claim 2 characterised in that the control device is adapted to reduce the output power to a value in the range of between 2% and 50% of the original output power when the signal of the measuring and calculating device indicates that the first derivative of the impedance or the ohmic resistance exceeds the positive threshold.

4. A high frequency current application apparatus as set forth in claim 1 characterised in that the measuring and calculating device is adapted to derive the parameters required for ascertaining impedance or ohmic resistance solely by means of a measuring circuit which is independent of the therapeutic circuit.

5. A high frequency current application apparatus as set forth in claim 4 characterised in that the control device is adapted to reduce the output power to a value in the range of between 0% and 50% of the original output power when the signal of the measuring and calculating device indicates that the first derivative of the impedance or the ohmic resistance exceeds the positive threshold.

6. A high frequency current application apparatus as set forth in claim 4 characterised in that the separate measuring circuit operates at a frequency different from the working frequency of the therapeutic high frequency current source.

7. A high frequency current application apparatus as set forth in claim 1 characterised in that the measuring and calculating device is adapted to form the first derivative in respect of time of the characteristic of the impedance or ohmic resistance from two measurement values which occur in succession in time of the impedance or the ohmic resistance.

8. A high frequency current application apparatus as set forth in claim 1 characterised in that the measuring and calculating device is adapted to calculate an average value of a number of measurement values which occur in succession in respect of time of the impedance or ohmic resistance and to form the first derivative in respect of time of the characteristic of the impedance or ohmic resistance from two measurement values which occur in succession in time of the impedance or the ohmic resistance.

9. A high frequency current application apparatus as set forth in claim 1 characterised in that the control device is adapted to reduce the output power when the signal of the measuring and calculating device indicates that the first derivative in respect of time of the characteristic of the impedance or ohmic resistance exceeds a value in the range of between 5 ohms/second and 50 ohms/second.

10. A high frequency current application apparatus as set forth in claim 1 characterised in that the control device is adapted to continuously reduce the output power over a short period of time.

11. A high frequency current application apparatus as set forth in claim 10 characterised in that the period of time is between 0.1 second and 5 seconds long.

12. A high frequency current application apparatus as set forth in claim 1 characterised in that the control device is adapted to maintain the reduced output power independently of the characteristic in respect of time of the impedance or resistance for a minimum time.

13. A high frequency current application apparatus as set forth in claim 12 characterised in that the minimum time is between 1 second and 10 seconds long.

14. A high frequency current application apparatus as set forth in claim 13 characterised in that the control device is adapted to use the first derivative of the characteristic in respect of time of the impedance or resistance for further control of power delivery again after expiry of the minimum time.

15. A high frequency current application apparatus as set forth in claim 1 characterised in that the control device is adapted to increase the output power again when the signal of the measuring and calculating device indicates that the first derivative in respect of time of the characteristic of impedance or ohmic resistance exceeds a value in the range of between minus 10 ohms/second and minus 0.1 ohm/second.

16. A high frequency current application apparatus as set forth in claim 9 characterised in that different threshold values can be selected for different kinds of tissue.

17. A high frequency current application apparatus as set forth in claim 1 characterised in that the control device is adapted to continuously return the output power to the original power over a short period of time.

18. A high frequency current application apparatus as set forth in claim 17 characterised in that the period of time is between 0.1 second and 5 seconds long.

19. A high frequency current application apparatus as set forth in claim 1 characterised in that the high frequency generator, the measuring and calculating device and the control device are disposed in a common housing.

20. A high frequency current application apparatus as set forth in claim 1 characterised in that the two electrodes between which impedance or ohmic resistance measurement is effected are arranged on a shank which is to be introduced into the body tissue.

21. A high frequency current application apparatus as set forth in claim 1 characterised in that the two electrodes between which impedance or ohmic resistance measurement is effected are arranged on two different shanks which are both to be introduced into the body tissue.

22. A high frequency current application apparatus as set forth in claim 1 characterised in that at least one of the two electrodes between which impedance or ohmic resistance measurement is effected is formed from a plurality of separate elements which are either arranged on the same shank or on different shanks and which are at the same electrical potential by an electrically conducting connection.

23. A high frequency current application apparatus as set forth in claim 1 characterised in that one of the two electrodes between which impedance or ohmic resistance measurement is effected is a neutral electrode which is to be applied to the surface of the skin.

24. A high frequency current application apparatus as set forth in claim 23 characterised in that the neutral electrode is formed from a plurality of separate elements which are to be applied to different surfaces of the skin and which are at the same electrical potential by an electrically conducting connection.

25. A high frequency application apparatus as set forth in claim 1 characterised in that the high frequency application apparatus has a control connection for an external pump connected to the electrodes which are introduced into the body tissue.

26. A high frequency application apparatus as set forth in claim 25 characterised in that the high frequency application apparatus is connected to a pump which is adapted to convey fluid into body tissue to be treated.

27. A high frequency application apparatus as set forth in claim 25 characterised in that the control device is adapted to cause the pump to be switched on when the control device detects a threat of tissue desiccation.

28. A high frequency application apparatus as set forth in claim 27 characterised in that the control device is adapted to actuate the external pump in such a way that fluid is conveyed into the treatment volume exclusively through those electrodes between which the control device has detected a threat of tissue desiccation.

29. A high frequency application apparatus as set forth in claim 27 characterised in that the control device is adapted to simultaneously cause the pump to be switched on and the output power to be reduced.

30. A high frequency application apparatus as set forth in claim 25 characterised in that the control device is adapted to actuate the pump in such a way that the pump conveys a previously defined amount of fluid into the treatment volume, wherein the amount of fluid is such that it approximately corresponds to the amount of previously vaporised tissue water.

31. A high frequency application apparatus as set forth in claim 26 characterised in that the pump is adapted to operate with a constant delivery and the control device is adapted to deactivate the pump again upon adequate tissue rehydration.

32. A high frequency application apparatus as set forth in claim 31 characterised in that the control device is adapted to cause deactivation of the pump and restoration of the output power to the original power at the same moment in time.

33. A high frequency application apparatus as set forth in claim 26 characterised in that the fluid is sterile physiological saline solution.

34. A high frequency application apparatus as set forth in claim 26 characterised in that the fluid is sterile water.

35. A high frequency current application apparatus for thermal sclerosing of body tissue, comprising a high frequency generator to which there are connected at least two electrodes which are configured for contact with body tissue, and a measuring and calculating device which is adapted to ascertain from at least two of the parameters current strength, voltage, phase relationship and active power the impedance or the ohmic resistance between the two electrodes, between which a therapeutic high frequency current respectively flows, or to ascertain same by means of a measuring circuit independent of the therapeutic circuit, and a control device connected to the measuring and calculating device for varying the electrical output power of the high frequency generator, characterised in that the measuring and calculating device is adapted during a high frequency current application to form the first derivative from the characteristic in respect of time of the impedance or the ohmic resistance and to deliver a value dependent on the value of the first derivative, and the control device is adapted to significantly reduce the output power when the signal of the measuring and calculating device indicates that the derivative in respect of time of the impedance or the ohmic resistance exceeds a positive threshold which is characteristic for a threatening tissue desiccation and to restore the output power to the original power again when the signal of the measuring and calculating device indicates that the first derivative of the characteristic in respect of time of the impedance or ohmic resistance exceeds in the direction of positive values a negative threshold which is characteristic of adequate rehydration of the body tissue.

36. A high frequency current application apparatus as set forth in claim 15 characterised in that different threshold values can be selected for different kinds of tissue.

* * * * *